(12) United States Patent
Pretorius et al.

(10) Patent No.: US 11,357,822 B2
(45) Date of Patent: Jun. 14, 2022

(54) LIPOPOLYSACCHARIDE-BINDING PROTEIN FOR USE IN A METHOD OF TREATING ALZHEIMER'S DISEASE

(71) Applicant: Stellenbosch University, Stellenbosch (ZA)

(72) Inventors: Etheresia Pretorius, Stellenbosch (ZA); Douglas Bruce Kell, Manchester (GB)

(73) Assignee: Stellenbosch University, Stellenbosch (ZA)

(*) Notice: Subject to any disclaimer, the term of this patent is extended or adjusted under 35 U.S.C. 154(b) by 10 days.

(21) Appl. No.: 16/640,039

(22) PCT Filed: Oct. 4, 2017

(86) PCT No.: PCT/IB2017/056118
§ 371 (c)(1),
(2) Date: Feb. 18, 2020

(87) PCT Pub. No.: WO2019/034922
PCT Pub. Date: Feb. 21, 2019

(65) Prior Publication Data
US 2021/0187068 A1 Jun. 24, 2021

(30) Foreign Application Priority Data
Aug. 16, 2017 (ZA) .................................. 2017/05548

(51) Int. Cl.
*A61K 38/17* (2006.01)
*A61P 25/28* (2006.01)

(52) U.S. Cl.
CPC .......... *A61K 38/1709* (2013.01); *A61P 25/28* (2018.01)

(58) Field of Classification Search
CPC ...... A61K 38/1709; A61K 38/17; A61P 25/28
See application file for complete search history.

(56) References Cited

U.S. PATENT DOCUMENTS

2009/0304695 A1* 12/2009 He .......................... C07K 16/30
424/135.1

FOREIGN PATENT DOCUMENTS

| WO | 1999/055731 A1 | 11/1999 |
| WO | 2007/023148 A2 | 3/2007 |

OTHER PUBLICATIONS

UniProt P18428, pp. 1-13. Integrated into UniProtKB/Swiss-Proton Nov. 1, 1990. (Year: 1990).*
Rudinger J, "Characteristics of the amino acids as components of a peptide hormone sequence," Peptide Hormones, JA Parsons Edition, University Park Press, Jun. 1976, pp. 1-7. (Year: 1976).*
"Designing Custom Peptides," from SIGMA Genosys, pp. 1-2. Accessed Dec. 16, 2004. (Year: 2004).*
Schinzel R, Drueckes P, "The phosphate recognition site of *Escherichia coli* maltodextrin phosphorylase," FEBS, Jul. 1991, 286(1,2): 125-128. (Year: 1991).*
Berendsen HJC, "A Glimpse of the Holy Grail?" Science, 1998, 282: 642-643. (Year: 1998).*
Voet D, Voet JG, Biochemistry, Second Edition, John Wiley & Sons, Inc., 1995, pp. 235-241. (Year: 1995).*
Ngo JT, Marks J, Karplus M, "Computational Complexity, Protein Structure Prediction, and the Levinthal Paradox," The Protein Folding Problem and Tertiary Structure Prediction, K. Merc Jr. and S. Le Grand Edition, 1994, pp. 491-495. (Year: 1994).*
Bradley CM, Barrick D, "Limits of Cooperativity in a Structurally Modular Protein: Response of the Notch Ankyrin Domain to Analogous Alanine Substitutions in Each Repeat," J. Mol. Biol., 2002, 324: 373-386. (Year: 2002).*
Yampolsky et al., "The Exchangeabilityof Amino Acids in Proteins," Genetics, 2005, 170: 1459-1472. (Year: 2005).*
Nervous System from Merck Manual, pp. 1-3. Accessed Aug. 24, 2021. (Year: 2021).*
Neurodegenerative disorder from Merck Manual, pp. 1-4. Accessed Aug. 24, 2021. (Year: 2021).*
Neurological disorders from Merck Manual, pp. 1-3. Accessed Aug. 24, 2021. (Year: 2021).*
Balu DT, "The NMDA Receptor and Schizophrenia: From Pathophysiology to Treatment," Adv. Pharmacol., 2016, 76: 351-382. (Year: 2016).*
Beyetal, "Phencyclidine Intoxication and Adverse Effects: A Clinical and Pharmacological Review of an Illicit Drug," The California Journal of Emergency Medicine VIII, 2007, pp. 9-14. (Year: 2007).*
Zhang et al, "Dysfunction of NMDA receptors in Alzheimer's disease," Neurol. Sci., 2016, 37: 1039-1047. (Year: 2016).*
International Search Report, International Patent Application No. PCT/IB2017/056118, dated Apr. 15, 2018, 5 pages.
Written Opinion of the International Searching Authority, International Patent Application No. PCT/IB2017/056118, dated Feb. 21, 2019, 8 pages.
Bester, Janette, et al., "Viscoelastic and Ultrastructural Characteristics of Whole Blood and Plasma in Alzheimer-type Dementia, and the Possible Role of Bacterial Lipopolysaccharides (LPS)." Oncotarget, Oct. 10, 2015, vol. 6, No. 34, pp. 35284-35303.
Pretorius, Etheresia, et al., "Lipopolysaccharide-Binding Protein (LBP) Can Reverse The Amyloid State of Fibrin Seen or Induced in Parkinson's Disease: Implications For Its Aetiology ." Apr. 4, 2017, <https://doi.org/10.1101/124180>, 21 pages.

* cited by examiner

*Primary Examiner* — Julie Ha
(74) *Attorney, Agent, or Firm* — Fitch, Even, Tabin & Flannery LLP (57) ABSTRACT

A method for treating a subject suffering from Alzheimer's disease is provided. The method includes administering to the subject a therapeutically effective amount of lipopolysaccharide-binding protein (LBP). A composition including a therapeutically effective amount of LBP is also provided.

5 Claims, 3 Drawing Sheets
Specification includes a Sequence Listing.

SEQUENCE LISTING

```
<160> NUMBER OF SEQ ID NOS: 1

<210> SEQ ID NO 1
<211> LENGTH: 481
<212> TYPE: PRT
<213> ORGANISM: Homo sapiens

<400> SEQUENCE: 1

Met Gly Ala Leu Ala Arg Ala Leu Pro Ser Ile Leu Leu Ala Leu Leu
1               5                   10                  15

Leu Thr Ser Thr Pro Glu Ala Leu Gly Ala Asn Pro Gly Leu Val Ala
            20                  25                  30
```

Arg Ile Thr Asp Lys Gly Leu Gln Tyr Ala Ala Gln Glu Gly Leu Leu
    35                  40                  45

Ala Leu Gln Ser Glu Leu Leu Arg Ile Thr Leu Pro Asp Phe Thr Gly
50                  55                  60

Asp Leu Arg Ile Pro His Val Gly Arg Gly Arg Tyr Glu Phe His Ser
65                  70                  75                  80

Leu Asn Ile His Ser Cys Glu Leu Leu His Ser Ala Leu Arg Pro Val
                85                  90                  95

Pro Gly Gln Gly Leu Ser Leu Ser Ile Ser Asp Ser Ser Ile Arg Val
                100                 105                 110

Gln Gly Arg Trp Lys Val Arg Lys Ser Phe Phe Lys Leu Gln Gly Ser
                115                 120                 125

Phe Asp Val Ser Val Lys Gly Ile Ser Ile Ser Val Asn Leu Leu Leu
                130                 135                 140

Gly Ser Glu Ser Ser Gly Arg Pro Thr Val Thr Ala Ser Ser Cys Ser
145                 150                 155                 160

Ser Asp Ile Ala Asp Val Glu Val Asp Met Ser Gly Asp Leu Gly Trp
                165                 170                 175

Leu Leu Asn Leu Phe His Asn Gln Ile Glu Ser Lys Phe Gln Lys Val
                180                 185                 190

Leu Glu Ser Arg Ile Cys Glu Met Ile Gln Lys Ser Val Ser Ser Asp
                195                 200                 205

Leu Gln Pro Tyr Leu Gln Thr Leu Pro Val Thr Thr Glu Ile Asp Ser
                210                 215                 220

Phe Ala Asp Ile Asp Tyr Ser Leu Val Glu Ala Pro Arg Ala Thr Ala
225                 230                 235                 240

Gln Met Leu Glu Val Met Phe Lys Gly Glu Ile Phe His Arg Asn His
                245                 250                 255

Arg Ser Pro Val Thr Leu Leu Ala Ala Val Met Ser Leu Pro Glu Glu
                260                 265                 270

His Asn Lys Met Val Tyr Phe Ala Ile Ser Asp Tyr Val Phe Asn Thr
                275                 280                 285

Ala Ser Leu Val Tyr His Glu Glu Gly Tyr Leu Asn Phe Ser Ile Thr
                290                 295                 300

Asp Asp Met Ile Pro Pro Asp Ser Asn Ile Arg Leu Thr Thr Lys Ser
305                 310                 315                 320

Phe Arg Pro Phe Val Pro Arg Leu Ala Arg Leu Tyr Pro Asn Met Asn
                325                 330                 335

Leu Glu Leu Gln Gly Ser Val Pro Ser Ala Pro Leu Leu Asn Phe Ser
                340                 345                 350

Pro Gly Asn Leu Ser Val Asp Pro Tyr Met Glu Ile Asp Ala Phe Val
                355                 360                 365

Leu Leu Pro Ser Ser Ser Lys Glu Pro Val Phe Arg Leu Ser Val Ala
370                 375                 380

Thr Asn Val Ser Ala Thr Leu Thr Phe Asn Thr Ser Lys Ile Thr Gly
385                 390                 395                 400

Phe Leu Lys Pro Gly Lys Val Lys Val Glu Leu Lys Glu Ser Lys Val
                405                 410                 415

Gly Leu Phe Asn Ala Glu Leu Leu Glu Ala Leu Leu Asn Tyr Tyr Ile
                420                 425                 430

Leu Asn Thr Phe Tyr Pro Lys Phe Asn Asp Lys Leu Ala Glu Gly Phe
                435                 440                 445

```
                                                -continued

Pro Leu Pro Leu Leu Lys Arg Val Gln Leu Tyr Asp Leu Gly Leu Gln
    450                 455                 460

Ile His Lys Asp Phe Leu Phe Leu Gly Ala Asn Val Gln Tyr Met Arg
465                 470                 475                 480

Val
```

LIPOPOLYSACCHARIDE-BINDING PROTEIN FOR USE IN A METHOD OF TREATING ALZHEIMER'S DISEASE

CROSS-REFERENCE TO RELATED APPLICATIONS

This application is a U.S. national phase application filed under 35 U.S.C. § 371 of International Application PCT/IB2017/056118, filed Oct. 4, 2017, which is based upon and claims the benefit of priority from the prior South African Provisional Application No. 2017/05548, filed Aug. 16, 2017.

REFERENCE TO A SEQUENCE LISTING

The Sequence Listing associated with this application is filed in electronic format via EFS-Web and is hereby incorporated into the specification in its entirety. The name of the text file containing the Sequence Listing is "Sequence_Listing". The size of the text file is 5.0 KB, and the file was created on Feb. 18, 2020.

FIELD OF THE INVENTION

This invention relates to the field of Alzheimer's disease, more particularly to a method and composition for preventing or treating Alzheimer's disease.

BACKGROUND TO THE INVENTION

Alzheimer's disease (AD) is a common age-related progressive neurodegenerative disorder resulting from the loss of dopaminergic neurons. The progression of AD is accompanied by many observable changes, both molecular and physiological. These include oxidative stress, neuroinflammation and (more proximal to cognitive decline) the death of neuronal and other cells.

The disease is characterised by the formation, deposition and accumulation of a fibres of beta-amyloid protein or Aβ, which forms extracellular amyloid plaques in the brains of patients with AD. The accumulation and persistence of the Aβ fibrils is a likely major causative factor of AD pathogenesis.

AD is also characterised by the presence of numerous neurofibrillary tangles, consisting of paired helical filaments which abnormally accumulate in the neuronal cytoplasm. AD is further characterized by the deposition of amyloid in the walls of blood vessels, both in the brain parenchyma and in the walls of meningeal vessels that lie outside the brain.

Despite significant progress made in understanding the processes which lead to AD and the manner in which the disease progresses, there are currently no methods or therapeutic agents capable of treating AD or slowing the neuronal degeneration associated with the disease. There is therefore a need for a new and effective method of treating AD and other neuroinflammatory disorders.

The preceding discussion of the background to the invention is intended only to facilitate an understanding of the present invention. It should be appreciated that the discussion is not an acknowledgment or admission that any of the material referred to was part of the common general knowledge in the art as at the priority date of the application.

SUMMARY OF THE INVENTION

In accordance with a first aspect of this invention there is provided a method of treating a subject suffering from Alzheimer's disease, the method comprising administering to the subject a therapeutically effective amount of lipopolysaccharide-binding protein (LBP) or a functional fragment thereof having lipopolysaccharide binding activity, wherein the LBP or fragment has an amino acid sequence with at least 80% sequence identity to SEQ ID NO: 1 or to any subsequence thereof.

The LBP or fragment may be administered parenterally, such as by way of intravenous, intramuscular, subcutaneous, intradermal, intramuscular, intra-articular, intra-synovial, intrasternal, intrathecal, intrahepatic, intralesional or intracranial injection or infusion techniques.

The LBP or fragment may be administered to attain a blood level of LBP in the subject of from about 1 ng/L to about 100 µg/L, from about 1 ng/L to about 10 µg/L, from about 1 ng/L to about 1 µg/L, from about 1 ng/L to about 100 ng/L, from about 1 ng/L to about 10 ng/L, or preferably about 4 ng/L.

The therapeutically effective amount may be selectable from about 5 ng to about 500 µg, from about 5 ng to about 50 µg, from about 5 ng to about 5 µg, from about 5 ng to about 500 ng, from about 5 ng to about 50 ng, or preferably about 20 ng.

The LBP or fragment may be administered to the subject at a dosage amount of from about 0.07 ng/kg/day to about 7 µg/kg/day, from about 0.07 ng/kg/day to about 700 ng/kg/day, from about 0.07 ng/kg/day to about 70 ng/kg/day, from about 0.07 ng/kg/day to about 0.7 ng/kg/day, or preferably about 0.30 ng/kg/day.

The LBP or fragment may be administered to the subject at a frequency selected from the group consisting of: once daily, twice daily, three times daily, four times daily, once weekly, once every two days, once every three days, once every four days, once every five days, and once every six days.

The method may reduce, reverse or prevent amyloid formation, beta-amyloid fibre formation, or beta amyloid plaque formation in the blood and/or brain of the subject.

The method may reduce the onset of Alzheimer's disease or slow down its progression in the subject.

In accordance with a second aspect of the invention there is provided a composition comprising lipopolysaccharide binding protein (LBP) or a functional fragment thereof having lipopolysaccharide binding activity and a pharmaceutically acceptable diluent, adjuvant or carrier for use in treating a subject suffering from Alzheimer's disease, wherein the LBP or fragment has an amino acid sequence with at least 80% sequence identity to SEQ ID NO: 1 or to any subsequence thereof.

The LBP or fragment may be present in the composition in a therapeutically effective amount, which may be a unit dosage amount selectable from about 5 ng to about 500 µg, from about 5 ng to about 50 µg, from about 5 ng to about 5 µg, from about 5 ng to about 500 ng, from about 5 ng to about 50 ng, or preferably about 20 ng.

The composition may contain the LBP or fragment in a dosage amount sufficient to attain an LBP blood level in the subject of from about 1 ng/L to about 100 µg/L, from about 1 ng/L to about 10 µg/L, from about 1 ng/L to about 1 µg/L, from about 1 ng/L to about 100 ng/L, from about 1 ng/L to about 10 ng/L, or preferably about 4 ng/L, when administered to the subject. The dosage amount may be from about 0.07 ng/kg/day to about 7 µg/kg/day, from about 0.07 ng/kg/day to about 700 ng/kg/day, from about 0.07 ng/kg/day to about 70 ng/kg/day, from about 0.07 ng/kg/day to about 0.7 ng/kg/day, or preferably about 0.30 ng/kg/day.

The composition may be formulated for parenteral administration, preferably for intravenous, intramuscular, subcutaneous, intradermal, intramuscular, intra-articular, intrasynovial, intrasternal, intrathecal, intrahepatic, intralesional or intracranial injection or infusion.

The composition may be formulated for administration at a frequency selected from the group consisting of: once daily, twice daily, three times daily, four times daily, once weekly, once every two days, once every three days, once every four days, once every five days, and once every six days.

The composition may reduce, reverse or prevent amyloid formation, beta-amyloid fibre formation, or beta amyloid plaque formation in the blood and/or brain of the subject.

The composition may reduce the onset of Alzheimer's disease or slow down its progression in the subject.

In accordance with a third aspect of the invention there is provided a use of lipopolysaccharide binding protein (LBP) or a functional fragment thereof having lipopolysaccharide binding activity in the manufacture of a medicament for treating a subject suffering from Alzheimer's disease, wherein the LBP or fragment has an amino acid sequence with at least 80% sequence identity to SEQ ID NO: 1 or to any subsequence thereof.

The LBP or fragment may be present in the medicament in a therapeutically effective amount, which may be a unit dosage amount selectable from about 5 ng to about 500 µg, from about 5 ng to about 50 µg, from about 5 ng to about 5 µg, from about 5 ng to about 500 ng, from about 5 ng to about 50 ng, or preferably about 20 ng.

The medicament may be in a dosage amount sufficient to attain an LBP or fragment blood level in the subject of from about 1 ng/L to about 100 µg/L, from about 1 ng/L to about 10 µg/L, from about 1 ng/L to about 1 µg/L, from about 1 ng/L to about 100 ng/L, from about 1 ng/L to about 10 ng/L, or preferably about 4 ng/L, when administered to the subject The dosage amount may be from about 0.07 ng/kg/day to about 7 µg/kg/day, from about 0.07 ng/kg/day to about 700 ng/kg/day, from about 0.07 ng/kg/day to about 70 ng/kg/day, from about 0.07 ng/kg/day to about 0.7 ng/kg/day, or preferably about 0.30 ng/kg/day.

The medicament may be formulated for parenteral administration, preferably for intravenous, intramuscular, subcutaneous, intradermal, intramuscular, intra-articular, intrasynovial, intrasternal, intrathecal, intrahepatic, intralesional or intracranial injection or infusion.

The medicament may be formulated for administration at a frequency selected from the group consisting of: once daily, twice daily, three times daily, four times daily, once weekly, once every two days, once every three days, once every four days, once every five days, and once every six days.

The medicament may reduce the onset of Alzheimer's disease or slow down its progression in the subject.

In accordance with a fourth aspect of the invention there is provided a kit for treating a subject suffering from Alzheimer's disease, the kit including a composition comprising lipopolysaccharide binding protein (LBP) or a functional fragment thereof as defined above and instructions on the use of the composition.

The instructions may indicate a dosage regimen sufficient to attain an LBP or fragment blood level in the subject of from about 1 ng/L to about 100 µg/L, from about 1 ng/L to about 10 µg/L, from about 1 ng/L to about 1 µg/L, from about 1 ng/L to about 100 ng/L, from about 1 ng/L to about 10 ng/L, or preferably about 4 ng/L.

The instructions may indicate a dosage regimen of LBP which may be selectable from about 0.07 ng/kg/day to about 7 µg/kg/day, from about 0.07 ng/kg/day to about 700 ng/kg/day, from about 0.07 ng/kg/day to about 70 ng/kg/day, from about 0.07 ng/kg/day to about 0.7 ng/kg/day, or preferably about 0.30 ng/kg/day.

The dosage regimen may include a frequency of administration of the composition selected from the group consisting of: once daily, twice daily, three times daily, four times daily, once weekly, once every two days, once every three days, once every four days, once every five days, and once every six days.

DETAILED DESCRIPTION OF THE INVENTION

Throughout the specification unless the content requires otherwise the word 'comprise' or variations such as 'comprises' or 'comprising' will be understood to imply the inclusion of a stated integer or group of integers but not the exclusion of any other integer or group of integers.

The term "pharmaceutically acceptable" means physiologically tolerable and suitable for use in humans or animals without producing an adverse, allergic or other untoward reaction when administered to a human or animal, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art.

The term "identity" as used herein means the identity between two amino acid sequences compared to each other within a corresponding sequence region having approximately the same amount of amino acids. For example, the identity of a full-length sequence of two amino acid sequences may be determined. Furthermore, a shorter amino acid sequence can be compared with a longer sequence and the identity between the two sequences will relate to the identity between the short sequence and a section of the longer sequence of approximately the same number of amino acids. In this way the identity of a truncated fragment of an LBP polypeptide can be compared to a full LBP polypeptide over the length of the truncated fragment. The amino acid sequences to be compared may differ in several positions which do not alter the biological function or structure of the polypeptides. Such "variants" may include amino acid substitutions, deletions, combinations or insertions of one or more positions in the amino acid sequences, but they still function in a substantially similar manner to the protein defined in SEQ ID NO: 1.

The term "functional fragment" as it relates to LBP, refers to a protein being a variant of LBP but having a substantially similar function or activity. Throughout the specification, the term "lipopolysaccharide (LPS)-binding protein" and its abbreviation "LBP" is understood to include a functional fragment thereof.

The term "subsequence" means a fragment or part of a full length sequence, such as an amino acid sequence. A subsequence of an LBP amino acid sequence has one or more amino acids less than the full length LBP amino acid sequence (e.g. one or more internal or terminal amino acid deletions from either the N- or C-terminal). Subsequences therefore can be any length up to the full length native molecule, provided the length is at least one amino acid less than the full length native molecule. Subsequences can vary in size. For example a subsequence of an LBP can be as small as an epitope capable of binding LPS (i.e., about five amino acids) up to a polypeptide that is one amino acid less than the entire length of an LBP polypeptide.

A "therapeutically effective amount" refers to an amount sufficient to improve in any way the state of health of the subject.

"Treating" as applied to a subject means reducing the progression of a disease, reducing or suppressing at least one of its symptoms or complications, or improving in any way the state of health of a treated subject. In the context of the present invention, this includes reducing the progression of Alzheimer's disease, reducing or suppressing at least one of its symptoms or complications, or improving in any way the state of health of human or animal subjects. "Treated" as applied to a chemical or biological sample which is "treated" with a chemical or biological entity merely refers to the application of the chemical or biological entity to the sample.

Lipopolysaccharide (LPS)-binding protein (LBP) is a 60 kD glycoprotein synthesized in the liver and present in normal human serum. LBP belongs to the group of plasma proteins called acute phase proteins, including C-reactive protein, fibrinogen and serum amyloid A, that increase in concentration in response to infectious, inflammatory and toxic mediators. LBP binds to bacterial LPS and promotes an immune response by presenting the LPS to cell surface pattern recognition receptors. Human LBP has the amino acid sequence provided below in Table 1 as SEQ ID NO: 1. This sequence can also be found on the Uniprot online protein database under reference number P18428, accessible at www.uniprot.org/uniprot/P18428.

TABLE 1

Amino acid sequence of human lipopolysaccharide (LPS)-binding protein (LBP) (SEQ ID NO: 1)

```
        10         20         30         40
MGALARALPS ILLALLLTST PEALGANPGL VARITDKGLQ 50         60         70         80
YAAQEGLLAL QSELLRITLP DFTGDLRIPH VGRGRYEFHS 90        100        110        120
LNIHSCELLH SALRPVPGQG LSLSISDSSI RVQGRWKVRK
```

TABLE 1-continued

Amino acid sequence of human lipopolysaccharide (LPS)-binding protein (LBP) (SEQ ID NO: 1)

```
       130        140        150        160
SFFKLQGSFD VSVKGISISV NLLLGSESSG RPTVTASSCS 170        180        190        200
SDIADVEVDM SGDLGWLLNL FHNQIESKFQ KVLESRICEM 210        220        230        240
IQKSVSSDLQ PYLQTLPVTT EIDSFADIDY SLVEAPRATA 250        260        270        280
QMLEVMFKGE IFHRNHRSPV TLLAAVMSLP EEHNKMVYFA 290        300        310        320
ISDYVFNTAS LVYHEEGYLN FSITDDMIPP DSNIRLTTKS 330        340        350        360
FRPFVPRLAR LYPNMNLELQ GSVPSAPLLN FSPGNLSVDP 370        380        390        400
YMEIDAFVLL PSSSKEPVFR LSVATNVSAT LTFNTSKITG 410        420        430        440
FLKPGKVKVE LKESKVGLFN AELLEALLNY YILNTFYPKF 450        460        470        480
NDKLAEGFPL PLLKRVQLYD LGLQIHKDFL FLGANVQYMR V
```

The invention provides a method of treating a subject suffering from Alzheimer's disease, involving administering to the subject a therapeutically effective amount of LBP or a functional fragment thereof having lipopolysaccharide binding activity, in which the LBP or fragment has an amino acid sequence with at least 80% sequence identity to SEQ ID NO: 1 or to any subsequence thereof. The invention further provides a composition including LBP or the functional fragment and a pharmaceutically acceptable diluent, adjuvant or carrier for use in the method of treatment.

In some embodiments, the LBP can have an amino acid sequence that has at least 81%, 82%, 83%, 84%, 85%, 86%, 87%, 88%, 89%, 90%, 91%, 92%, 93%, 94%, 95%, 96%, 97%, 98%, 99% or 100% sequence identity with SEQ ID NO: 1 or to any subsequence thereof.

The method can include administering the therapeutically effective amount of lipopolysaccharide-binding protein (LBP) to the subject parenterally, such as by way of intravenous, intramuscular, subcutaneous, intradermal, intramuscular, intra-articular, intra-synovial, intrasternal, intrathecal, intrahepatic, intralesional or intracranial injection or infusion techniques. The LBP can be administered to attain a blood level of LBP in the subject of from about 1 ng/L to about 100 µg/L, from about 1 ng/L to about 10 µg/L, from about 1 ng/L to about 1 µg/L, from about 1 ng/L to about 100 ng/L, from about 1 ng/L to about 10 ng/L, or preferably about 4 ng/L. For an average 70 kg human subject having an average blood volume of 5 litres, a blood level of 4 ng/L LBP amounts to about 20 ng of LBP.

The therapeutically effective amount can be a dosage of from about 0.07 ng/kg/day to about 7 µg/kg/day, from about 0.07 ng/kg/day to about 700 ng/kg/day, from about 0.07 ng/kg/day to about 70 ng/kg/day, from about 0.07 ng/kg/day to about 0.7 ng/kg/day, or preferably about 0.30 ng/kg/day. This can be a unit dosage amount of LBP selectable from about 5 ng to about 500 µg, from about 5 ng to about 50 µg, from about 5 ng to about 5 µg, from about 5 ng to about 500 ng, from about 5 ng to about 50 ng, or preferably about 20 ng.

Throughout the specification, "kg" units in the "ng/kg/day" dosage amount refers to the subject's body weight.

The method can include administering a dosage of the LBP once or multiple times daily. For example in one embodiment the LBP is administered once daily. In another embodiment the LBP is administered twice daily. In yet another embodiment the LBP is administered three times daily. In another embodiment the LBP is administered four times daily. In further embodiments, the LBP can be administered once weekly. In further embodiments, the dosage may be administered once weekly, once every two days, once every three days, once every four days, once every five days, or once every six days. The dosage can be adjusted to maintain a desired blood level of LBP in the subject.

In some embodiments, the method can reduce, reverse or prevent amyloid formation, beta-amyloid fibre formation, or beta amyloid plaque formation in the blood and/or brain of the subject. The method can also lower systemic levels of inflammation and restore healthy blood coagulation. In some particular embodiments, the method can reduce the onset of Alzheimer's disease or slow down its progression in the subject.

The LBP can be human or animal LBP.

The composition including LBP or a functional fragment thereof having lipopolysaccharide binding activity and a pharmaceutically acceptable diluent, adjuvant or carrier for use in the above-defined method of treating Alzheimer's disease can include a therapeutically effective amount of LBP. This may be a unit dosage amount of from about 5 ng to about 500 µg, from about 5 ng to about 50 µg, from about 5 ng to about 5 µg, from about 5 ng to about 500 ng, from about 5 ng to about 50 ng, or preferably about 20 ng.

The composition can contain LBP in a dosage amount sufficient to attain an LBP blood level in the subject of from about 1 ng/L to about 100 µg/L, from about 1 ng/L to about 10 µg/L, from about 1 ng/L to about 1 µg/L, from about 1 ng/L to about 100 ng/L, from about 1 ng/L to about 10 ng/L, or preferably about 4 ng/L, when administered to the subject. The dosage amount required to achieve these blood levels can be an amount of LBP of from about 0.07 ng/kg/day to about 7 µg/kg/day, from about 0.07 ng/kg/day to about 700 ng/kg/day, from about 0.07 ng/kg/day to about 70 ng/kg/day, from about 0.07 ng/kg/day to about 0.7 ng/kg/day, or most preferably about 0.30 ng/kg/day.

The composition can be formulated for parenteral administration, such as by intravenous (IV), intramuscular (IM), subcutaneous (SC) or intradermal (ID) administration. The formulation can be prepared according to the following procedure. The LBP is dissolved, suspended or emulsified either in an aqueous medium (such as distilled water, physiological saline or Ringer's solution) or in an oily medium (such as olive oil, sesame seed oil, cottonseed oil, corn oil or propylene glycol), optionally containing one or more of a surfactant (such as Tween 80, polyethylene glycol, carboxymethylcellulose or sodium alginate), a preserving agent (such as methyl p-hydroxybenzoate, propyl p-hydroxybenzoate, benzyl alcohol, chlorobutanol or phenol), an isotonicity agent (such as sodium chloride, glycerol, sorbitol or glucose), a solubilising agent (such as sodium salicylate or sodium acetate), a stabiliser (such as human serum albumin), or another suitable additive or adjuvant.

The composition can alternatively be prepared for oral administration. A solid pharmaceutical form can be prepared by the following procedure: an excipient (such as lactose, sucrose, starch or mannitol), a disintegrant (such as calcium carbonate, calcium carboxymethylcellulose, alginic acid, sodium carboxymethylcellulose, colloidal silicon dioxide, sodium croscarmellose, Crospovidone, guar gum, magnesium aluminium silicate, microcrystalline cellulose, cellulose powder, pregelatinised starch, sodium alginate or starch glycolate), a binder (such as alpha-starch, gum arabic, carboxymethylcellulose, polyvinylpyrrolidone, hydroxypropylcellulose, alginic acid, carbomer, dextrin, ethylcellulose, sodium alginate, maltodextrin, liquid glucose, magnesium aluminium silicate, hydroxyethylcellulose, methylcellulose or guar gum) and a lubricant (for example talc, magnesium stearate or polyethylene 6000) are combined with a solid form of LBP and the mixture tableted. If necessary, the tablet can be coated via known techniques, in order to mask the taste or to allow enteric dissolution or sustained release of the LBP. Pharmaceutically acceptable colorants may be added (for example yellow iron oxide, red iron oxide or quinoline yellow lake).

Liquid pharmaceutical forms for oral administration, which can include solutions, suspensions and emulsions, can be obtained by dissolving the LBP in aqueous medium, and optionally adding a solubilising agent such as ethanol, propylene glycol or any other pharmaceutically acceptable non-aqueous solvent. The aqueous suspensions for oral use can be obtained by dispersing finely divided LBP, which may be freeze dried, in water with a viscous product, such as a natural or synthetic gum or resin, methylcellulose or sodium carboxymethylcellulose.

The composition of the present invention can be administered once or multiple times daily. For example in one embodiment the composition is administered once daily. In another embodiment the composition is administered twice daily. In yet another embodiment the composition is administered three times daily. In another embodiment the composition is administered four times daily. In further embodiments, the composition can be for once weekly administration. In further embodiments, the composition is administered once weekly, once every two days, once every three days, once every four days, once every five days, or once every six days. Administration of the composition can be at a selected frequency required to maintain a desired blood level of LBP in the subject.

In some embodiments, the composition can reduce, reverse or prevent amyloid formation, beta-amyloid fibre formation, or beta amyloid plaque formation in the blood and/or brain of the subject. The composition can also lower systemic levels of inflammation and restore healthy blood coagulation. In some particular embodiments, the composition can reduce the onset of Alzheimer's disease or slow down its progression in the subject.

The composition can be provided in a kit for treating a subject suffering from Alzheimer's disease. The kit can include instructions on the use and administration of the composition. For example, the instructions can indicate a dosage regimen sufficient to attain an LBP blood level in the subject of from about 1 ng/L to about 100 µg/L, from about 1 ng/L to about 10 µg/L, from about 1 ng/L to about 1 µg/L, from about 1 ng/L to about 100 ng/L, from about 1 ng/L to about 10 ng/L, or preferably about 4 ng/L.

The dosage regimen included in the instructions may be selectable from about 0.07 ng/kg/day to about 7 µg/kg/day, from about 0.07 ng/kg/day to about 700 ng/kg/day, from about 0.07 ng/kg/day to about 70 ng/kg/day, from about 0.07 ng/kg/day to about 0.7 ng/kg/day, or preferably about 0.30 ng/kg/day.

The invention extends to the use of lipopolysaccharide binding protein (LBP) or a functional fragment thereof having lipopolysaccharide binding activity in the manufacture of a medicament for treating a subject suffering from Alzheimer's disease. The medicament can be provided by the composition defined above in which the LBP or fragment has an amino acid sequence with at least 80% sequence identity to SEQ ID NO: 1 or to any subsequence thereof.

In some embodiments, the LBP can have an amino acid sequence that has at least 81%, 82%, 83%, 84%, 85%, 86%, 87%, 88%, 89%, 90%, 91%, 92%, 93%, 94%, 95%, 96%, 97%, 98%, 99% or 100% sequence identity with SEQ ID NO: 1 or to any subsequence thereof.

The method and composition of the invention can be used in humans or animals with existing Alzheimer's disease (AD), including those at early or late stages of the disease, preferably at an early stage of the disease. The method and composition may not necessarily cure the subject who has the disease but may delay or slow the progression or prevent further progression of the disease, thereby improving the subject's condition. The LBP can also be administered to those who do not have symptoms of AD but who would normally develop AD or be at increased risk of developing AD. Treatment with the method or composition can also include delaying the development of the disease in a subject that will ultimately develop all symptoms of AD or would be at risk for the disease due to age, familial history, genetic or chromosomal abnormalities, and/or due to the presence of one or more biological markers for the disease. By delaying the onset of the disease, the method and composition can prevent the subject from contracting AD during the period in which the subject would normally have contracted the disease, or reduce the rate of development of the disease or some of its effects. By slowing down the progression of AD, the LBP prevents the subject from contracting one or more complications associated with AD during the period in which the subject would normally have contracted the complications, or reduce the rate of development of one or more complications associated with AD. The method may also be administered to a subject believed to be predisposed to AD.

The invention will now be described in more detail by way of the following non-limiting examples.

EXAMPLES

Materials and Methods

Low levels (final concentration: 4 ng·L$^{-1}$) of LPS-binding protein was added to platelet poor plasma (PPP), containing mostly fibrinogen. To the PPP was added ThT (thioflavin T) followed by human thrombin to create an extensive fibrin fibre clot. Fluorescence was measured before and after the addition of LPS-binding protein using confocal fluorescent microscopy (or super resolution confocal microscope) to determine if LPS-binding protein reversed amyloid formation in Alzheimer's disease patient blood plasma. ThT binds to open hydrophobic areas on fibrin protein fibres and fluoresces when in contact with amyloidogenic proteins. If fluorescence is present as seen with ThT, amyloid is present. The more amyloid protein is present the more fluorescent areas will be visible in the clots. Clot structure was studied with scanning electron microscopy to see if LPS-binding protein does indeed reverse the abnormal hypercoagulated clot structure as seen in Alzheimer's disease blood before treatment with LPS-binding protein; and if the aberrant clotting could be reversed with LPS-binding protein or restored to the structure of a healthy clot. The presence of ThT binding or the presence of hypercoagulable matted clot areas compared between treated and untreated Alzheimer's disease clots were quantified and compared to healthy clots. As metric the coefficient of variation or CV was used.

Results

Table 2 shows the demographics of the Alzheimer's disease population and the healthy population whose blood were analysed in this study. Transferrin, % saturation of iron and serum ferritin were also measured and these values, particularly the serum ferritin concentration, were used as an indication of the level of systemic inflammation. In healthy individuals serum ferritin is low, whereas in the Alzheimer's disease population it is 3× higher.

TABLE 2

Demographics for the healthy and the Alzheimer's disease individuals.

| | Alzheimer's disease | Healthy individuals |
|---|---|---|
| Gender | 17 F:3 M | 6 F; 4 M |
| Age | 80.5 (±12.1) | 71 (±13.6) |
| Iron μM | 11.20 (±5.02) | 18.75 (±4.62) |
| Transferrin g · L$^{-1}$ | 2.15 (±0.47) | 2.35 (±0.31) |
| % Saturation | 24.00 (±10.79) | 30 (±7.85) |
| Serum Ferritin ng · mL$^{-1}$ | 163.88 (±163.88) | 53.5 (±44.50) |

Table 3 shows results for the analysis of the clots using both scanning electron microscopy (SEM) and also Airyscan™ confocal microscopy.

Clot Structure as Seen with Confocal Microscopy:

An Airyscan™ confocal microscope was used for the analysis, although any suitable confocal microscope could have been employed. Airyscan™ produces fluorescence images of higher resolution than standard confocal microscopes. Quantification of fluorescent marker binding (ThT) was assessed by determining the variance between (black) background and the presence of fluorescent pixels for ThT (fluorescent marker) in the clots. Increased binding correlated with increased fluorescence which correlated with increased amyloid formation in blood which correlated with aberrant clot structure. The histogram function in ImageJ (FIJI) was used to calculate the coefficient of variation (CV) (as SD/mean) of the histogram of different pixel intensities as a metric to quantify and discriminate between clots of healthy (age-controlled) naïve PPP and clots from Alzheimer's individuals.

Clot Structure as Seen with Scanning Electron Microscopy

A healthy clot looks like a bowl of spaghetti with elongated fibrin fibres. In Alzheimer's Disease, this changes to a matted hypercoagulated clot. The CV calculation described above was applied to SEM clots in which the fibrin fibres of healthy individuals have dark and light areas, due to the elongated fibres, whereas with increased hypercoagulability the clots become matted and more uniform in colour. This difference in structure was used as a metric where increased hypercoagulability correlated with increased uniformly formed mats. CVs were also calculated from SEM images.

Table 3 shows the CV results calculated from the above description. There is a significantly different P-value that was noted for both methods (SEM and Airyscan™ results) between controls and Alzheimer's disease clots. CVs were calculated from the data shown at the bottom of each histogram. Sample analysis was performed by the Mann-Whitney U test, using the STATSDIRECT (version 2.8.0) software.

TABLE 3

Data for Alzheimer's disease and healthy individuals showing the coefficients
of variation (CV) of the intensity of the pixels in the clot images.

| DATA ANALYSIS FOR SCANNING ELECTRON MICROSCOPY AND AIRYSCAN™ | | |
|---|---|---|
| ALZHEIMER'S DISEASE DATA Coefficient of variation (CV) | | HEALTHY INDIVIDUAL DATA Coefficient of variation (CV) |
| Naïve AD | AD treated with LBP | Naïve controls |
| SEM ANALYSIS: MEDIAN AND SD | | |
| 0.50 (± 0.2) | 0.93 (±0.16) | 0.84 (±0.10) |
| AIRYSCAN™ ANALYSIS: MEDIAN AND SD | | |
| 1.11 (±0.39) | 0.82 (±0.4) | 0.74 (±1.11) |

| CHOICE OF SAMPLES | TEST USED | P-VALUE |
|---|---|---|
| SCANNING ELECTRON MICROSCOPY | | |
| Analysis between naïve AD and naïve controls | Mann-Whitney | Two sided P = 0.0004 |
| Analysis between naïve AD and AD treated with LBP | Paired T-test | Two sided P < 0.0001 |
| Analysis between AD treated with LBP and naïve controls | Mann-Whitney | Two-sided P = 0.145 |
| AIRYSCAN™ TECHNOLOGY | | |
| Analysis between naïve AD and naïve controls | Mann-Whitney | Two sided P = 0.097 |
| Analysis between naïve AD and AD treated with LBP | Paired T-test | Two sided P = 0.0019 |
| Analysis between AD treated with LBP and naïve controls | Mann-Whitney | Two-sided P = 0.99 |

Experiments were performed in which plasma from Alzheimer disease patients was treated with LPS-binding protein. These experiments demonstrated that aberrant clot structure could be reversed so that it had an appearance resembling clots from healthy individuals.

Figure 1:
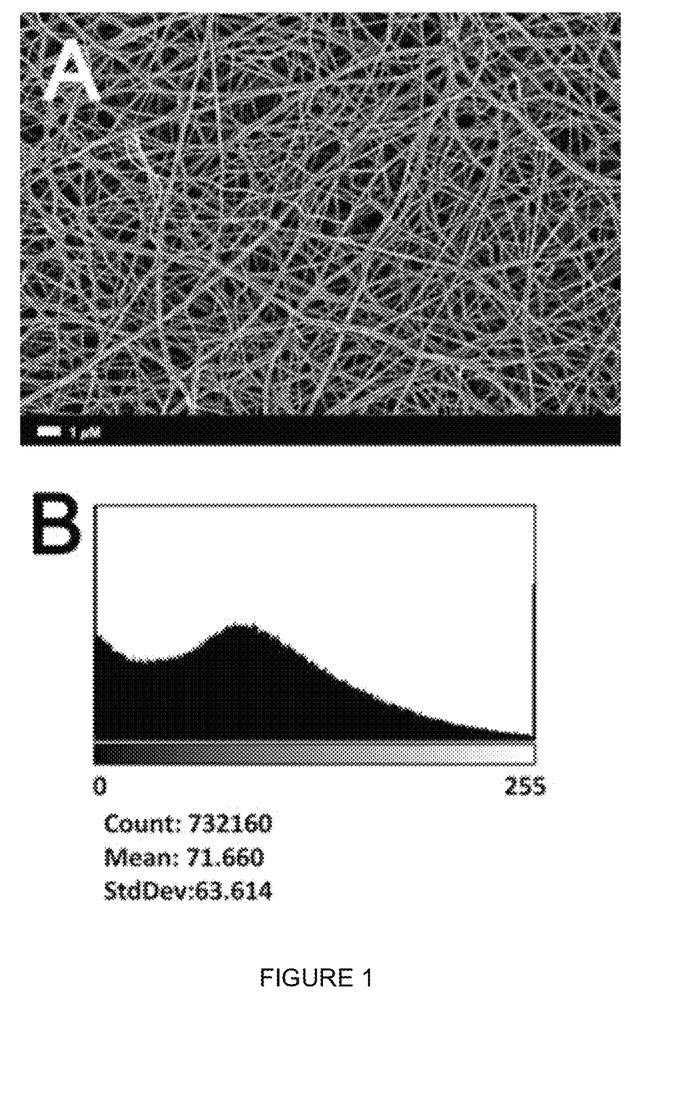
FIG. 1: A) Clot structure from a representative healthy individual as seen with SEM. All clots were created by adding thrombin to platelet poor plasma. B) Representative histogram of the 8-bit intensity for the SEM clot shown in A.
Figure 2:
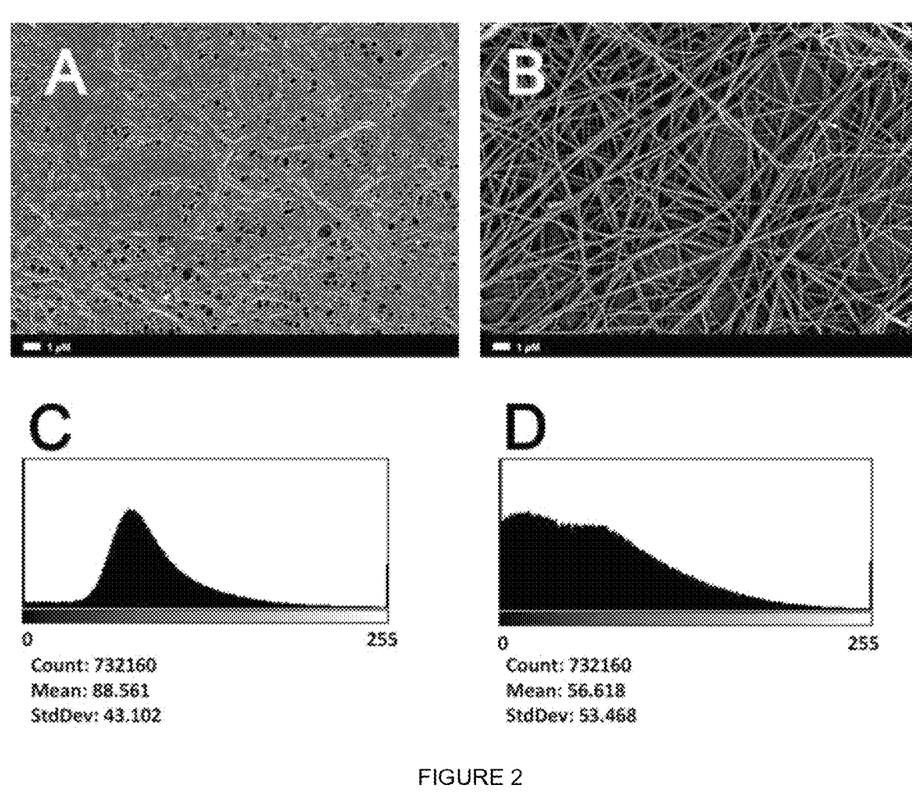
FIG. 2: A) Naïve clot structure from a representative Alzheimer's individual as seen with SEM. B) The same sample treated with LPS-binding protein. Representative C and D) Representative histograms of the 8-bit intensity for the SEM clot shown in A and B.
Figure 3:
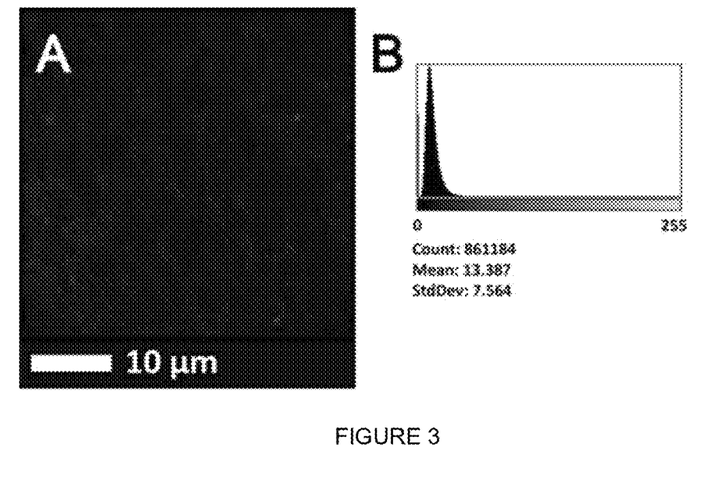
FIG. 3: A) Clot structure from a representative healthy individual as seen with Airyscan™ super-resolution confocal microscopy. All clots were created by adding thrombin to platelet poor plasma. B) Representative histogram of the 8-bit intensity for the Airyscan™ clot shown in A.
Figure 4:
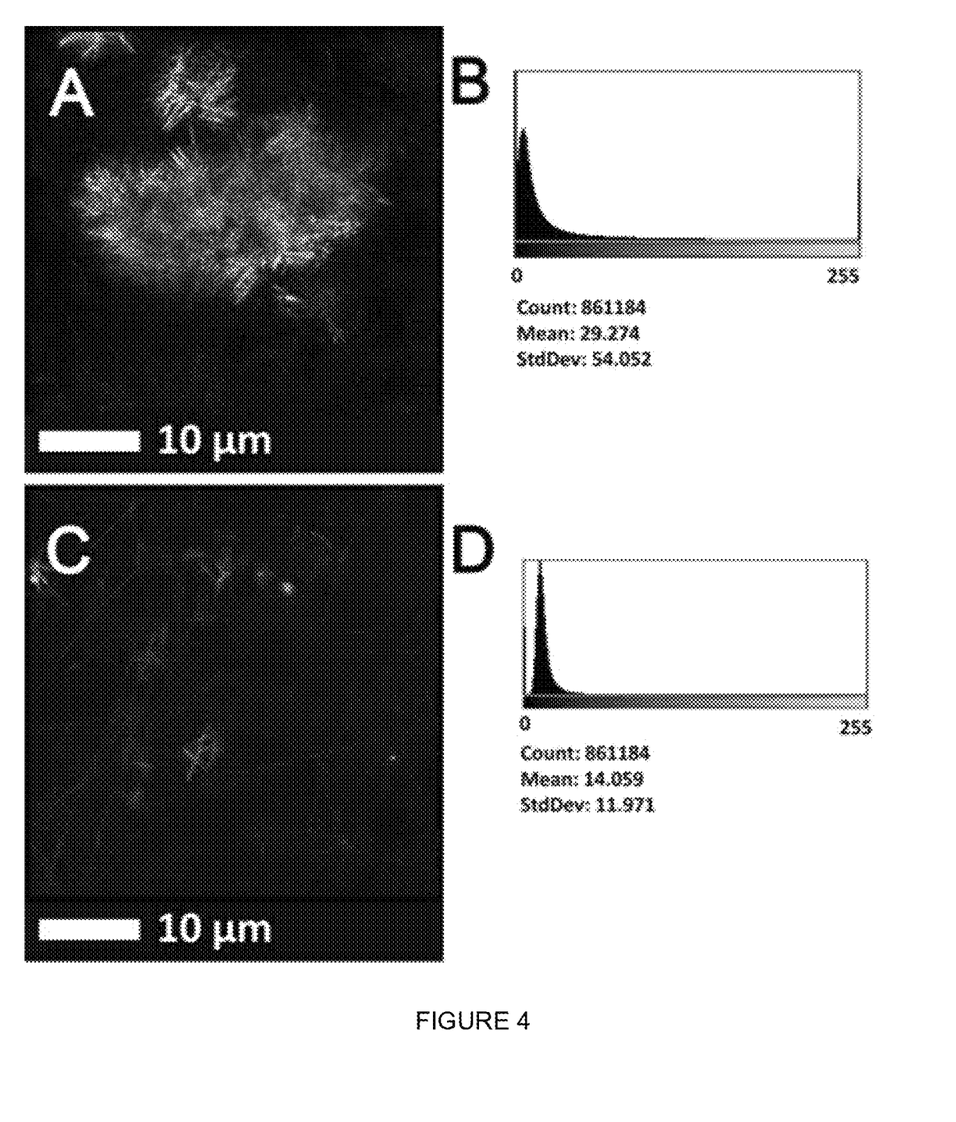
FIG. 4: A) Naïve clot structure from a representative Alzheimer's individual as seen with airyscan super-resolution confocal microscopy. B) The same sample treated with LPS-binding protein. Representative C and D) Representative histograms of the 8-bit intensity for the Airyscan™ clot shown in A and B.

FIG. 1 gives an example of the clot structure from a representative healthy individual as seen with SEM (A) and also the representative histogram (B) of the 8-bit intensity for the SEM clot shown in FIG. 1A, generated from the histogram functioning ImageJ. FIG. 2 shows before (A) and after (B) images of Alzheimer's disease blood treated with LPS-binding protein, and the representative histograms (generated from ImageJ). FIGS. 3 and 4 show representative micrographs using Airyscan™ confocal microscopy to study clots from healthy individuals (FIG. 3) where there is little to no binding of ThT to amyloid fibrin(ogen) proteins. FIGS. 4A and 4B show a representative Alzheimer disease clot with the added ThT marker that binds to amyloid fibrin (ogen) and the representative histograms from which the CV were generated. FIGS. 4C and 4D, show a representative clot after plasma was treated with LPS-binding protein and in which fluorescence is greatly reduced.

The results show that LPS-binding protein added in low concentrations to plasma or whole blood of Alzheimer's disease patients has the ability to reverse aberrant clotting that causes a hypercoagulable state in these individuals. This hypercoagulable state is a symptom of systemic inflammation. By mopping or binding systemic LPS in the blood of Alzheimer's disease patients through the administration of LPS-binding protein, not only is aberrant blood clotting prevented, but levels of LPS in their brains can also be reduced.

The treatment regimen that follows from this data is one which would maintain a level of LBP in the blood between 1 ng/L and 100 µg/L, preferably at about 4 ng/L in order to reduce, reverse or prevent amyloid formation, beta-amyloid fibre formation, or beta amyloid plaque formation in the blood and/or brain of Alzheimer's disease sufferers. This treatment regimen can be a unit dosage amount of LBP selectable from about 5 ng to about 500 µg, preferably about 20 ng, administered at suitable time intervals to achieve the required blood LBP level. Since LBP is naturally occurring, normalising blood levels of LBP to between 1 ng/L and 100 µg/L, and preferably at about 4 ng/L, through administration can treat Alzheimer's disease, delay the onset of the disease, or slow down its progression in the subject.

The invention claimed is:

1. A method of treating a subject suffering from Alzheimer's disease, the method comprising administering to the subject a therapeutically effective amount of lipopolysaccharide-binding protein (LBP), wherein the LBP has an amino acid sequence with at least 98% sequence identity to SEQ ID NO: 1 and has lipopolysaccharide-binding activity.

2. The method as claimed in claim 1, wherein the therapeutically effective amount is from about 5 ng to about 500 µg.

3. The method as claimed in claim 1, wherein the LBP is administered to the subject at a frequency selected from the group consisting of: once daily, twice daily, three times daily, four times daily, once weekly, once every two days, once every three days, once every four days, once every five days, and once every six days.

4. The method as claimed in claim 1, wherein the LBP is administered to the subject at a dosage of from about 0.07 ng/kg/day to about 7 µg/kg/day.

5. The method as claimed in claim 1, wherein the LBP has an amino acid sequence which is identical to SEQ ID NO: 1.

* * * * *